US00PP14730P3

(12) United States Plant Patent
Jones

(10) Patent No.: US PP14,730 P3
(45) Date of Patent: Apr. 27, 2004

(54) NEMESIA PLANT NAMED 'PENCAND'

(50) Latin Name: *Nemesia*
Varietal Denomination: Pencand

(76) Inventor: Sidney James Jones, Penhow Nursery Carrow Hill, St. Bridges Netherwent Magar Calaicot, South Wales, NP26 3AU (GB)

( * ) Notice: Subject to any disclaimer, the term of this patent is extended or adjusted under 35 U.S.C. 154(b) by 0 days.

(21) Appl. No.: 10/036,204

(22) Filed: Dec. 28, 2001

(65) Prior Publication Data

US 2003/0126658 P1 Jul. 3, 2003

(51) Int. Cl.[7] ..... A01H 5/00

(52) U.S. Cl. ..... Plt./263

(58) Field of Search ..... Plt./263

*Primary Examiner*—Kent Bell

(57) ABSTRACT

A new and distinct cultivar of Nemesia plant named 'Pencand' that is characterized by a trailing, compact, mounding habit, dense upright spikes of fragrant white to pink flowers with yellow centers, and light green leaves. In combination these characteristics set 'Pencand' apart from all other existing varieties of Nemesia known to the inventor.

2 Drawing Sheets

Genus/species: Nemesia hybrid.
Denomination: 'Pencand'.

BACKGROUND OF THE INVENTION

The present invention relates to a new and distinct cultivar of Nemesia plant known botanically as Nemesia hybrid and that will be referred to hereinafter by the cultivar name 'Pencand'.

The new Nemesia is a product of a planned breeding program conducted by the Inventor in Netherwent, Wales. The breeding program objectives were to improve upon well-known varieties such as *Nemesia denticulata* 'Confetti' (unpatented), *Nemesia caerulea* 'Innocence' (unpatented), *Nemesia caerulea* 'Joan Wilder' (unpatented), *Nemesia caerulea* 'Woodcote' (unpatented), and *Nemesia caerulea* 'Elliott's' (unpatented). The goals of the breeding program were to improve on plant habit by breeding plants that were more compact, with stiff, upright flower spikes, increase the size of the flower and the length of flowering time, improve the color range by producing clear colors, and produce plants that root readily and consistently from vegetative stem cuttings.

The new Nemesia originated from a cross-pollination made by the Inventor in 1996 of an unnamed and unpatented Nemesia hybrid, as the female, or seed, parent with an unnamed and unpatented Nemesia hybrid, as the male, or pollen, parent. The cultivar 'Pencand' was discovered and selected by the Inventor as a plant within the progeny from this cross-pollination in a controlled environment in Netherwent, Wales, in 1996.

'Pencand' is distinguishable from the parent plants by white to pink flowers with yellow center, a trailing, compact, mounding habit, and dense, upright fragrant flower spikes. The leaves are lanceolate in shape and exhibit thicker tissue than other Nemesia known to the inventor.

'Pencand' was first asexually propagated by the Inventor in 1997 in a cultivated area or Netherwent, Wales using vegetative stem cuttings and has shown that the unique features of this new Nemesia plant are stable and reproduced true to type in successive generations of asexual reproduction.

SUMMARY OF THE INVENTION

The following traits have been repeatedly observed and represent the distinguishing characteristics of 'Pencand'. In combinaton these traits set the new cultivar apart from all other existing varieties of Nemesia known to the inventor. 'Pencand' has not been tested under all possible conditions and phenotypic differences may be observed with variations in environmental, climatic, and cultural conditions, however, without any variance in genotype.

1. Nemesia 'Pencand' exhibits a trailing, mounding and compact habit.
2. Each individual plant of Nemesia 'Pencand' exhibits fragrant flowers that are white to pink in color with yellow centers.
3. Nemesia 'Pencand' exhibits dense upright flower spikes.
4. Nemesia 'Pencand' is floriferous and exhibits large, repeat-flowering heads.
5. Nemesia 'Pencand' is hardy to minus 5° Centigrade.
6. Nemesia 'Pencand' can be used in beds, borders and window boxes.

BRIEF DESCRIPTION OF THE DRAWINGS

The accompanying color drawings illustrate the overall appearance of the new Nemesia cultivar 'Pencand' showing the colors as true as it is reasonably possible to obtain in colored reproductions of this type. Colors in the drawings may differ from the color values cited in the detailed botanical description which accurately describe the actual colors of the new variety 'Pencand'. The plants are 4-months-old, in 10-centimeter containers and were grown under greenhouse conditions in San Diego, Calif.

The drawing on sheet 1 illustrates the entire plant's, habit and flowers from a side perspective.

The drawing on sheet 2 is a close-up view of the flower. The drawings were made using conventional photographic techniques. Although colors may appear different from actual colors due to light reflectance, they are as accurate as possible by conventional photography.

BOTANICAL DESCRIPTION OF THE PLANT

The following is a detailed description of the Nemesia plant named 'Pencand'. Data was collected in Arroyo Grande, Calif. from 4-month-old plants grown in 10-centimeter containers under greenhouse conditions. Phenotypic differences may be observed with variations in environmental, climatic, and cultural conditions. The color determinations are in accordance with The 2001 Royal Horticultural Society Colour Chart except where general color terms of ordinary dictionary significance are used. The growing requirements are similar to other Nemesia plants.

Botanical classification: Nemesia 'Pencand'.
Species: Hybrid.
Common name: Nemesia.
Use: Bedding, window box and patio plant.
Parentage: The parents of Nemesia 'Pencand' are unnamed Nemesia hybrids.
*Female parent.*—Unnamed Nemesia hybrid.
*Male parent.*—Unnamed Nemesia hybrid.
Propagation: Vegetative stem cuttings.
Sexuality: Hermaphrodite.
Growth habit: Compact, trailing and moundinghabit.
Plant dimensions: 18 cm. in height and 23 cm. in width.
Type: Hardy perennial.
Time to initiate roots: Approximately 16 days at temperatures of 21° Centigrade is needed to produce rooted cuttings.
Crop time: 4 months are required to produce a finished 10-centimeter product from a rooted cutting.
Root system: Numerous and fine.
Hardiness: Hardy to minus 5° Centigrade.
Disease and pest susceptibility or resistance: There are no disease problems known to the inventor other than what affects typical Nemesia.
Stem:
*Stem shape.*—Quadrilateral with ridges.
*Stem length.*—7 cm. in length.
*Stem diameter.*—3 mm. in diameter.
*Stem surface.*—Glabrous.
*Stem color.*—144A.
*Internode length.*—2–5 cm. between nodes.
*Branching.*—Ascending and freely branching Foliage:
*Leaf shape.*—Lanceolate.
*Leaf division.*—Simple.
*Apex.*—Acute.
*Base.*—Rounded.
*Margins.*—Crenate.
*Surface.*—Glabrous,
*Arrangement.*—Opposite.
*Leaf length.*—3 cm. in length.
*Leaf width.*—1.50 cm. in width.
*Leaf color* (*adaxial surface*).—137B.
*Leaf color* (*abaxial surface*).—138B.
*Attachment.*—Petiolate.
*Petiole dimensions.*—3 mm. in length and 2 mm. in diameter.
*Color of petiole* (*adaxial surface*).—137B.
*Color of petiole* (*abaxial surface*).—138B.
*Petiole surface* (*adaxial surface*).—Glabrous.
*Petiole surface* (*abaxial surface*).—Glabrous.
*Vein pattern.*—Parallel.
Flowers:
*Flowering season.*—Spring, summer and fall.
*Fragrance.*—Perfume fragrance.
*Self-cleaning or persistent.*—Self-cleaning.
*Inflorescence dimensions.*—4 cm. in length and 4 cm. in width.
*Type of inflorescence.*—Axillary raceme.
*Pedicel dimensions.*—9 mm. in length and 0.50 mm. in diameter.
*Pedicel surface.*—Glabrous and glossy.
*Pedicel color.*—144A.
*Peduncle dimensions.*—11.50 cm. in length and 3 mm. in diameter.
*Peduncle surface.*—Glabrous and glossy.
*Peduncle color.*—138B.
*Bud shape.*—Globular.
*Bud color.*—75C.
*Bud dimensions.*—3 mm. in length and 3 mm. in diameter.
*Flower color.*—Flower colors 75C and 75D and N155B are present on an individual plant.
*Flower shape.*—Personate.
*Palate color.*—14A in the center and 155A to the right and left sides of center.
*Nectary* (*located on underside of palate*).—4 mm. in width and 4 mm. in length.
*Color of nectary.*—163A.
*Throat color* (*upper surface*).—161C.
*Throat color* (*lower surface*).—163A.
*Surface of upper lip* (*adaxial and abaxial surfaces*).—Glabrous.
*Surface of lower lip* (*adaxial and abaxial surfaces*).—Glabrous.
*Lip margin* (*lower lip*).—Entire and undulate.
*Lip margin* (*upper lip*).—Entire.
*Lips.*—Two lips in number. Upper lip has four lobes and lower lip is not lobed.
*Lobes on upper lip fused or unfused.*—Fused.
*Upper and lower lips fused or unfused.*—Basally fused.
*Lip apex* (*upper lip*).—Each lobe has a rounded apex.
*Lip base* (*upper lip*).—Truncate.
*Lip apex* (*lower lip*).—Obtuse apex.
*Lip base* (*lower lip*).—Truncate.
*Flower dimensions.*—Flower is 1 cm. in depth, 1.5 cm. in length and 1.5 cm in width at the widest part.
*Lower lip dimensions.*—Lower lip is 8 mm. in length and 1 cm. in width.
*Upper lip dimensions.*—Upper lip is 8 mm. in length and 1.50 cm. in width.
*Lobe dimensions* (*upper lip*).—Each lobe is 8 mm. in length and 4.5 mm. in width.
*Upper lip color* (*adaxial and abaxial surfaces*).—Colors 75D and 75C and N155B are present on an individual plant.
*Lower lip color* (*adaxial and abaxial surfaces*).—Colors N155B, 75D and 75C are present on an individual plant.
*Flower spur dimensions.*—6 mm. in length and 2 mm. in diameter.
*Spur color.*—158A.
*Calyx dimensions.*—3 mm. in length and 6 mm. in width.

*Sepals.*—Five in number.
*Sepal surface.*—Glabrous and glossy.
*Sepal margin.*—Entire.
*Sepal apex.*—Acute.
*Sepal color* (*adaxial surfaces*).—137A.
*Sepal color* (*abaxial surfaces*).—137A.
*Lastingness of individual flower.*—Average of 2 weeks.

Reproductive organs:

*Stamens.*—Two in number with filaments curved around one another.
*Color of stamens.*—155A.
*Stamen dimensions.*—3 mm. in length and less than 1 mm. in diameter.
*Anther color.*—162A.
*Anther dimensions.*—Less than 0.50 mm. in length and less than 0.50 mm. in width.
*Pollen color.*—162A.
*Amount of pollen.*—Moderate amount.
*Pistil.*—One.
*Pistil color.*—155A.
*Pistil dimensions.*—0.25 mm. in length and 0.25 mm. in diameter.
*Ovary dimensions.*—0.50 mm. in length and 0.50 mm. in width.
*Ovary shape.*—Oval to round.
*Ovary position.*—Superior.
*Ovary color.*—145A.

Seed production:

*Quantity of seed.*—Approximately 15 fertile seeds per capsule.
*Capsules.*—Approximately 20 capsules per flowering spike, but this is markedly influenced by how many times the plant is pinched back.
*Capsule dimensions.*—12 mm. in length and 7 mm. in width.
*Capsule color.*—177D.
*Capsule surface.*—Glossy.
*Appearance of seed.*—Flattened and winged.
*Seed color.*—200D and wing 156D.
*Shape of seed.*—Oval.
*Seed dimensions.*—3 mm. in length and 2.5 mm. in width.

I claim:

1. A new and distinct cultivar of Nemesia plant named 'Pencand' as described and illustrated herein.

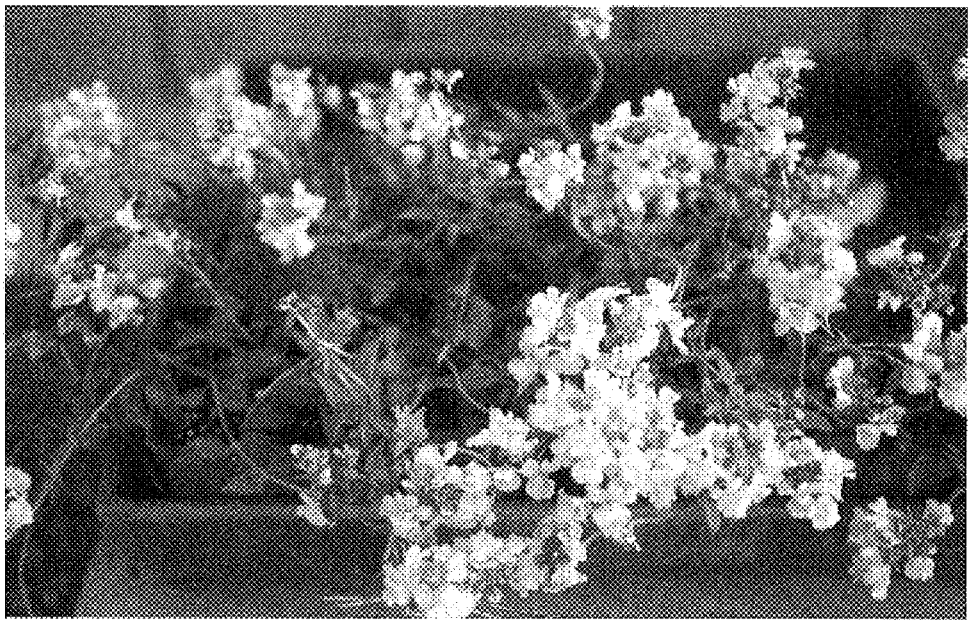

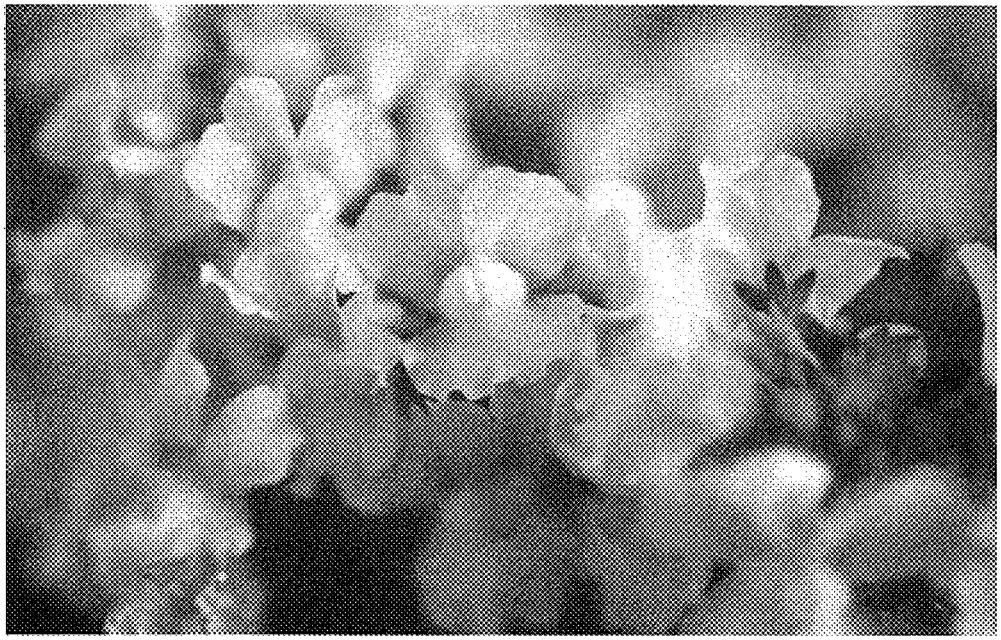

* * * * *